United States Patent
Gray et al.

(10) Patent No.: US 6,599,234 B1
(45) Date of Patent: Jul. 29, 2003

(54) HEATING OF MAGNETIC MATERIAL BY HYSTERESIS EFFECTS

(75) Inventors: Bruce Nathaniel Gray, Claremont (AU); Raffaele Cammarano, White Gum Valley (AU); Stephen Keith Jones, Leederville (AU)

(73) Assignee: Sirtex Medical Limited (AU)

( * ) Notice: Subject to any disclaimer, the term of this patent is extended or adjusted under 35 U.S.C. 154(b) by 0 days.

(21) Appl. No.: 09/914,714

(22) PCT Filed: Mar. 3, 2000

(86) PCT No.: PCT/AU00/00151
§ 371 (c)(1),
(2), (4) Date: Dec. 20, 2001

(87) PCT Pub. No.: WO00/52714
PCT Pub. Date: Sep. 8, 2000

(30) Foreign Application Priority Data

Mar. 3, 1999 (AU) .............................................. PP 8998

(51) Int. Cl.$^7$ .............................. A61F 2/00; A61B 17/52
(52) U.S. Cl. .......................................... 600/12; 607/103
(58) Field of Search ............................ 600/9–15, 1–8; 607/100–104; 424/322; 423/633

(56) References Cited

U.S. PATENT DOCUMENTS

| | | |
|---|---|---|
| 4,106,488 A | 8/1978 | Gordon |
| 4,303,636 A | 12/1981 | Gordon |
| 4,323,056 A | 4/1982 | Borrelli et al. |
| 4,545,368 A | 10/1985 | Rand et al. |
| 4,574,782 A | 3/1986 | Borrelli et al. |
| 4,662,359 A | 5/1987 | Gordon |
| 4,810,401 A | 3/1989 | Mair et al. |
| 4,983,159 A | 1/1991 | Rand |
| 5,181,021 A | 1/1993 | Lee et al. |
| 5,236,410 A | 8/1993 | Granov et al. |
| 5,411,730 A | 5/1995 | Kirpotin et al. |
| 5,429,583 A | 7/1995 | Paulus et al. |
| 5,468,210 A | 11/1995 | Matsui et al. |
| 6,149,576 A | 11/2000 | Gray et al. |
| 6,167,313 A | 12/2000 | Gray et al. |

FOREIGN PATENT DOCUMENTS

| | | |
|---|---|---|
| AU | 13106/97 | 8/1997 |
| AU | 26277/97 | 12/1997 |
| EP | 0 361 797 | 4/1990 |
| EP | 0 913 167 A2 | 5/1999 |
| FR | 2 508 802 | 1/1983 |
| GB | 895 179 | 5/1962 |
| WO | WO 94/12101 | 6/1994 |
| WO | WO 95/15786 | 6/1995 |
| WO | WO 97/743005 | 11/1997 |

OTHER PUBLICATIONS

Gilchrist et al., Selective Inductive Heating of Lymph Nodes, Annals of Surgery, Oct. 1957, vol. 146, No. 4, pp 596–606.

(List continued on next page.)

Primary Examiner—Samuel G. Gilbert
(74) Attorney, Agent, or Firm—Merchant & Gould P.C.

(57) ABSTRACT

A magnetic material having a magnetic heating efficiency of at least $4.5 \times 10^{-8}$ J.m/A.g in a cyclic magnetic field where the product of the amplitude and frequency of the applied field is less than or equal to $5 \times 10^8$ A/m.s, and the frequency of the applied filed is at least 20 kHz. The ideal magnetic material is characterized by a perfectly rectangular hysteresis loop, i.e. loop squareness of 1, with coercivity of 25 kA/m or less and high saturation magnetization. Preferably the magnetic material has a predominately cubic magnetic crystalline anisotropy. Preferably the magnetic material is a substituted magnetite ($Fe_3O_4$) or γ-ferric oxide ($\gamma Fe_2O_3$) crystalline lattice in which some of the iron atoms in that crystalline lattice have been substituted for one or more alternate metals atoms. Desirably, the metal atom is a member of the group: cobalt, zinc, nickel, manganese, magnesium, copper, chromium, gallium, cadmium.

35 Claims, 4 Drawing Sheets

OTHER PUBLICATIONS

Rand et al., Selective Radiofrequency Heating of Ferrosilicone Occluded Tissue: A Preliminary Report, Bull. Los Angeles Neurol. Soc. 41(4) pp 154–159, 1976.

Mosso et al., Ferromagnetic Silicone Vascular Occlusion: A Technic for Selective Infarction of Tumors and Organs, Ann. Of Surgery, Nov. 1972, pp 663–668.

Rand et al., Ferromagnetic Silicone Vascular in a Superconducting Magnetic Field Preliminary Report, Bull. Los Angeles Neurol. Soc., 1972, 37: pp. 67–74.

Rand et al., Thermomagnetic Surgery for Cancer, Journal of Surgical Research vol. 33, No. 3, Sep. 1982, pp 177–183.

Rand et al., Thermomagnetic Surgery for Cancer, Applied Biochemistry and Biotechnology 6, pp 265–272, 1981.

Gordon et al., Intracellular Hyperthermia A Biophysical Approach to Cancer Treatment Via Intracellular Temperature and Biophysical Alterations, Medical Hypotheses 5: pp 83–102, 1979.

Luderer et al, Glas–Ceramic–Mediated, Magnetic–Field–Induced Localized Hyperthermia: Response of a Murine Mammary Carcinoma, Radiation Research 94, pp 190–198, 1983.

Borrelli et al., Hysteresis heating for the treatment of tumours, Phys. Med. Biol. 1984, vol. 29, No. 5, pp. 487–494.

Matsuki et al., High Quality Soft Heating Method Utilizing Temperature Dependence of Permeability and Core Loss of Low Curie Temperature Ferrite, IEEE Transactions on Magnetics, vol. MAG–21, No. 5, Sep. 1985.

Matsuki et al., An Optimum Design of a Soft Heating System for Local Hyperthermia, IEEE Transactions on Magnetics, vol. MAG–23, No. 5, Sep. 1987.

Matsuki et al., Performance of Soft Heating for Locat Hyperthermia Using Temperature Sensitive Amorphous Metal Flakes, IEEE Trancactoins on Magnetics, vol. 25, No. 5, Sep. 1989.

Matsuski et al, Local Hyperthermia Based on Soft Heating Method Utilizing Temperature–Sensitive Ferrite Rod, IEEE Transactions on Magnetics, vol. 26, No. 5, Sep. 1990.

Yanada et al., Evaluation of Performance of Soft Heating Element for Local Hyperthermia, IEEE Translation Journal on Magnetics in Japan, vol. 6, No. 7, Jul. 1991.

Sato et al., Ferromagnetic Amorphous Metal Microcapsules for Intra–tissue Hyperthermia and Slow Release of Anti–Cancer Agents, Proc. 16th Annual Conference IEEE Embs. 1. pp. 131–133, 1992.

Sato et al., Development of a New Heating Device and an Exciting Coil for Interstitial hyperthermia, Proc. 16th Ann. Conf. IEEE, pp. 234–235, 1992.

Sato et al., The Development of Anticancer Agent Releasing Microcapsule Made of Ferromagnetic Amorphous Flakes for Intratissue Hyperthermia, IEEE Transactions on Magnetics, vol. 29, No. 6, Nov. 1993, pp. 3325–3330.

Matsuki et al., Temperature–sensitive amorphous magnetic flakes for intratissue hyperthermia, Materials Science and Engineering, A181/A182, 1994, pp. 1366–1368.

Bartlett et al., On the use of ferromagnetic microparticles in microwave and radio frequency hyperthermia, Journal of the Institution of Electronic and Radio Engineers, vol. 58, No. 4, pp. 197–201, Jun. 1988.

Suzuki et al., Studies on Liposomal Ferromagnetic Particles and a Technique of High Frequency Inductive Heating, J. Jpn. Soc. Cancer Ther. 25(11): pp. 2649–2658, Nov. 1990.

Chan et al., Synthesis and evaluation of colloidal magnetic iron oxides for the site–specific radiofrequency–induced hyperthermia of cancer, Journal of Magnetism and Magnetic Materials 122, 1993, pp. 374–378.

Jordan et al., Inductive heating of ferrimagnetic particles and magnetic fluids: physical evaluation of their potential for hyperthermia, Int. J. Hypertermia, 1993, vol. 9, No. 1, pp. 51–68.

Jordan et al., Cellular uptake of magnetic fluid particles and their effects on human adenocarcinoma cells exposed to AC magnetic fields in vitro, Int. J. Hyperthermia, 1996, vol. 12, No. 6, pp. 705–722.

Mitsumori, Development of intra–arterial hyperthermia using a dextran–magnetite complex, Int. J. Hyperthermia, 1994, vol. 10, No. 6, pp. 785–793.

Mitsumori et al., Targeted Hyperthermia using Dextran Magnetite Complex: A New Treatment Modality for Liver Tumors, Hepato–Gastroenterology 43, 1996, pp. 1431–1437.

Shinkai et al., Antibody–conjugated magnetoliposomes for targeting cancer cells and their application in hyperthermia, Biotechnol. Appl. Biochem. 21, 1994, pp. 125–137.

Suzuki et al., Preparation and characteristics of magnetite–labelled antibody with the use of poly(ethylene glycol) derivatives, Biotechnol. Appl. Biochem. 21, pp. 335–345, 1995.

Shinkai et al., Intracellular Hyperthermia for Cancer Using Magnetite Cationic Liposomes: In vitro Study, Jpn. J. Cancer Res. 87, pp. 1179–1183, Nov. 1996.

Jones et al., Evaluation of ferromagnetic materials for low–frequency hysteresis heating of tumours, Phys. Med. Biol. 1992, vol. 37, No. 1, pp. 293–299.

Jordan et al., Magnetic Fluid Hyperthermia (MGH), Scientific and Clinical Applications of Magnetic Carriers, Plenum Press, New York, 1997, pp. 569–595.

Bacri et al., Use of Magnetic Nanoparticles for Thermolysis of Cells in a Ferrofluid, Scientific and Clinical Applications of Magnetic Carriers, Plenum Press, New York, 1997, pp. 597–606.

Chan et al., Physical Chemistry and in vivo Tissue Heating Properties of Colloidal Magnetic Iron Oxides with Increased Power Absorption Rates, Scientific and Clinical Applications of Magnetic Carriers, Plenum Press, New York, 1997, pp. 607–618.

Inductive heating of ferrimagnetic particles and magnetic fluids: physical evaluation of their potential for hyperthermia; Jordan et al.; Int. J. Hyperthermia, 1993, vol. 9, No. 1, pp. 51–68.

Evaluation of ferromagnetic materials for low–frequency hysteresis heating of tumours; Jones et al.; Phys. Med. Biol., 1992, vol. 37, No. 1, pp. 293–299.

Targeted Hyperthermia using Dextran Magnetite Complex: A New Treatment Modality for Liver Tumors; Mitsumori et al.; Hepato–Gastroenterology, 1996, vol. 43, Iss 12, pp 1431–1437.

Intrecellular Hyperthermia for Cancer Using Magnetite Cationic Liposomes: In vitro Study; Shinkai et al.; Jpn. J. Cancer Res., vol. 87, pp. 1179–1183, Nov. 1996.

International Search Report for PCT/AU97/00287.

Co–pending application, Serial No. 09/569,788, entitled Targeted Hysteresis Hyperthermia as a Method of Treating Diseased Tissue, filed May 12, 2000.

Koster. "Magnetic anisotropy of cobalt–doped gamma ferric oxide". *IEEE Transaction on Magnetics*, vol. MAG–8, No. 3, pp. 428–430 (Sep. 1, 1972).

Hergt. "Physical limits of hyperthermia using magnetite fine particles". *IEEE Transaction on Magnetics*, vol. 34, No. 5, pp. 3745–3754 (Sep. 1, 1998).

HEATING OF MAGNETIC MATERIAL BY HYSTERESIS EFFECTS

FIELD OF INVENTION

The present invention relates to magnetic materials. More particularly, the invention relates to magnetic materials that exhibit high magnetic hysteresis heating in a cyclic magnetic field.

BACKGROUND ART

Each time a ferromagnetic material is exposed to a magnetic field whose amplitude and/or direction varies cyclically in time a small amount of energy is dissipated as heat due to magnetic hysteresis effects. The more rapidly the field is cycled, the greater the rate at which heat is produced by the material. By improving the rate at which a magnetic material heats, it is possible to maximise the potential uses to which this technology may be applied.

One means that has been used to increase the rate at which heat is produced by a magnetic material is to apply a rotating magnetic field to that material rather than the more usual linear alternating field. In our earlier co-owned patent application ("Improved Targeted Hysteresis Hyperthermia for Treating Diseased Tissue"), we have shown that under certain conditions of magnetic field strength and frequency, rotating fields cause far greater heating of magnetic materials compared to a linear alternating field, hence greater heating efficiency is achieved.

Another means to increase the rate at which heat is produced by a material is to improve the magnetic profile of the material and to select materials that display high heating efficiency. Thus, the need to maximise the heating efficiency of the magnetic particle is paramount.

Magnetic materials with an improved magnetic heating efficiency have application in any circumstances where localised heating of unexposed areas is required. For example, the materials may be used in such diverse situations as in rapid heating of cements or epoxies or in the treatment of cancer by hyperthermia therapy.

Where rapid heating of cements or epoxies is required for rapid curing without heating the nearby surfaces or objects, magnetic particles may be dispersed evenly throughout the cement or epoxy (only several parts per thousand would be needed) such that subsequent application of a cyclic magnetic field would cause uniform heating throughout the volume of the cement rather than just heating from the outside in.

In our previous patent applications, "Targeted Hysteresis Hyperthermia as a Method for Treating Diseased Tissue" and "Improved Targeted Hysteresis Hyperthermia for Treating Diseased Tissue", we disclose techniques for the localised heating of tumours using heat generated by small magnetic particles exposed to a time varying magnetic field. Magnetic particles are incorporated into biocompatible microcapsules that are administered in such a manner that they concentrate in the vascular network surrounding a tumour. A cyclic magnetic field is applied externally and heat from the microcapsules is conducted into the surrounding tumour tissue. Use of appropriately formulated microcapsules, magnetic field conditions and microcapsule dosage ensures that the tumours are heated to lethal temperatures, i.e. above about 42° C., whilst simultaneously sparing healthy tissue.

There are various ways to deliver the magnetic particles to tumours. For example, the magnetic particles can be administered by direct injection into the tumour tissue. In this way it is possible to get large quantities of material into the tumour. Hence, it may be possible to heat tumours to therapeutic levels using magnetic particles with inferior properties.

An alternative route of administration would demand delivery of the magnetic material preferably in microcapsule form via intra-vascular infusion to target the vascular network surrounding the tumour. This technique is preferred since it offers some significant advantages that improve the therapeutic effectiveness compared to direct injection into tumour. These advantages include the following:

(i) The less invasive nature of the delivery technique reduces the likelihood of inadvertent spreading of the cancer;

(ii) Target tumours do not need to be accurately located and exposed to enable injection of the particles;

(iii) A more optimal distribution of heating foci within the tumour will almost certainly obtain using the intra-vascular infusion technique; and (iv) It will be easier to treat a large number of small nodules such as often occurs in the case of metastastic liver cancer.

A feature of this route of administration is that a smaller number of particles are delivered to the diseased tissue compared to direct injection. Hence, improvements of the heating characteristics of the magnetic particles are extremely important in order to enable treatment of tumours using intra-vascular infusion.

We have previously specified the minimum operating constraints in terms of the strength of the applied field and its frequency assuming whole body exposure to the field. These stipulated field conditions for whole body exposure are that the frequency should be greater than about 10 kHz and the product of frequency and field strength should not exceed $5 \times 10^8$ A/m.s. We have also stipulated the minimum Magnetic Heating Efficiency (MHE) which must be achieved by the magnetic microcapsules subject to these conditions.

Certain commercially available materials do perform according to the stipulated conditions, however it is clear that any improvement in the heating efficiency subject to the imposed constraints, would significantly enhance the usefulness of this and other heating techniques.

The present invention seeks to provide a magnetic material with improved magnetic heating characteristics that can be used in diverse methods such as, but not limited to, the heating of cements and in the treatment of diseased tissue.

Throughout the specification, unless the context requires otherwise, the word "comprise" or variations such as "comprises" or "comprising", will be understood to imply the inclusion of a stated integer or group of integers but not the exclusion of any other integer or group of integers.

DISCLOSURE OF THE INVENTION

The present invention consists in a magnetic material having a magnetic heating efficiency of at least $4.5 \times 10^{-8}$ J.m/A.g in a cyclic magnetic field where the product of amplitude and frequency of the applied field is less than or equal to $5 \times 10^8$ A/m.s, and the frequency of the applied field is at least 20 kHz.

The ideal magnetic material is characterised by a perfectly rectangular hysteresis loop, i.e. loop squareness, defined by the ratio of the remanent to saturation magnetisation equal to 1, with coercivity of 25 kA/m or less and high saturation magnetisation. Such a situation is difficult to achieve with an array of randomly aligned particles as is the case when the magnetic materials are dispersed in compositions such as cement or epoxies or in biological tissues.

Preferably, the magnetic material has a predominantly cubic magnetocrystalline anisotropy. Particles with predominantly cubic magnetocrystalline anisotropy come closest to approaching the specified behaviour in a cyclic magnetic field since they can have a hysteresis loop squareness as high as 0.86.

For a random array of particles with other types of anisotropy (e.g. uniaxial anisotropy), loop squareness will not generally exceed 0.5. In considering arrays of particles with the same coercivity but different loop squareness, the maximum value of hysteresis work per cycle (i.e. either $W_a$ or $W_r$) will occur at a higher field for the array with the lower loop squareness. This means the magnetic heating efficiency for these particles will be less than for the particles with higher loop squareness.

Having regard for the field-frequency constraint discussed above, the maximum allowable applied field strength at 20 kHz is 25 kA/m (314 Oe), decreasing proportionately as frequency is increased beyond 20 kHz. Hence, the magnetic material desirably has a coercivity of less than 314 Oe. In addition, the remanence of the material should remain at a level that maximises the MHE.

In one embodiment of the present invention, there is provided a magnetic material having a coercivity of less than 314 Oe and a MHE of at least $4.5 \times 10^{-8}$ J.m/A.g in a cyclic magnetic field where the product of the amplitude and frequency of the applied field is not more than $5 \times 10^8$ A/m.s. and the frequency of the applied field is at least 20 kHz. In a preferred form of the invention the coercivity is less than 200 Oe.

The present invention should be understood to encompass any magnetic material that has the above mentioned characteristics. Preferably, the magnetic material is a substituted magnetite ($Fe_3O_4$) or γ-ferric oxide (γ-$Fe_2O_3$) crystalline lattice in which some of the iron atoms in that crystalline lattice have been substituted for one or more alternate metal atoms. Desirably, the metal atom is a member of the group: cobalt, zinc, nickel, manganese, magnesium, copper, chromium, gallium, cadmium. In this respect the substituting metal atom(s) may either be entirely selected from the same atomic species or a plurality of different metal atoms tan be incorporated into the crystalline lattice.

While it will be appreciated that any of the above mentioned metal atoms may be substituted for iron atoms in the magnetite ($Fe_3O_4$) or γ-ferric oxide (γ-$Fe_2O_3$) crystalline lattice, the magnetic material must be possessed of a predominantly cubic magnetocrystalline anisotropy. Preferably, the substituting metal atoms are dispersed in a substantially even manner throughout the crystalline lattice. When dispersed in such a manner the magnetic material tends to have a more predictable heating efficiency compared to the situation where the substituting metal atoms are all located in one region of the crystalline lattice.

In a highly specific form of the invention, the alternate metal atoms are cobalt atoms, and the magnetic material is a substituted magnetite ($Fe_3O_4$) or γ-ferric oxide (γ-$Fe_2O_3$) crystalline lattice. Where cobalt is the substituting metal atom the degree of substitution is preferably less than about 4% of the iron atoms in the crystalline lattice, more preferably in the range 0.2 and 3.5%.

In addition to being substituted preferably the magnetic material is provided in particulate form, with particles possessing equant morphology, such as simple cubic or spherical shapes, and being of a size between 20 nm and 1 μm.

To the extent that the present invention is to be used in the treatment of diseased tissue, there are several undesirable physiological effects that occur in response to sufficiently high rate of change of magnetic field, or dB/dt. These effectively impose limits on the frequency and strength of the magnetic field used in this application. These physiological responses are (i) cardiac muscle stimulation, (ii) peripheral nerve stimulation, and (iii) tissue heating due to eddy current generation.

To avoid cardiac muscle stimulation the frequency applied in the cyclic magnetic field should be greater than 10 kHz. Preferably, a frequency limit of 20 kHz is imposed to stay above the audible range, an important consideration for patient and operator comfort. Operating above 20 kHz is highly desirable since this frequency is above the audible range and so patient and operator comfort is substantially improved over that at lower frequencies where the noise may be at an uncomfortable level.

In addition to the above where the present invention is used in hyperthermic treatment of cancer, the MHE of that material is preferably such as to enable production of sufficient heat to raise the temperature of the cancerous tissue to 42° C., being the minimum temperature required for therapeutic effect. The scenario that demands the highest MHE from the magnetic material is likely to be the one where the magnetic material is delivered in the form of microcapsules to the site of the cancer via intra-arterial infusion.

The relatively small number of microcapsules that can be delivered via intra-arterial infusion means that each particle should be adapted to produce more heat in order to obtain the same therapeutic benefit. Preferably the magnetic material is to be capable of producing a minimum of 22.5 Watts per gram of material when exposed to the cyclic magnetic field.

Advantages gained by using a magnetic material within the scope of the present invention include:

1) improved therapeutic effectiveness by virtue of the fact that higher tumour temperatures can be reached more quickly (the effectiveness of hyperthermia therapy improves markedly as temperature is increased beyond 42° C.);
2) reduced toxic side effects because:
   i/. less microcapsules need to be used to achieve therapeutic heating in tumours (advantageous if the microcapsules have any intrinsic toxicity),
   ii/. more rapid heating of the tumour may be achieved which implicates less of the healthy tumour tissue immediately surrounding the tumour (the longer time required to heat the tumour the more the immediately surrounding tissue will be heated by thermal conduction);
3) increased likelihood of successful treatment especially for tumours that would otherwise be expected to only receive a marginal benefit;
4) the techniques have a wider applicability for the treatment of different types of cancer;
5) using reduced field strengths eases engineering difficulties associated with machine design;

In another embodiment there is provided a method for the production of a magnetic material within the scope of the present invention, the method comprising the steps of:

(i) dissolving a water-soluble salt of iron and one or more water-soluble salts of one or more alternate metal ions in aqueous solution;

(ii) co-precipitating hydroxides of iron and cobalt or each alternate metal ion from this solution;

(iii) treating the co-precipitated hydroxides in an aqueous medium with an oxidising agent which transforms the hydroxides into ferromagnetic iron oxides containing cobalt or each alternate metal ion;

(iv) separating the oxides from the aqueous medium, then drying and heating the oxides in an oxidising gaseous medium to a temperature not surpassing 500° C.

The oxide may be dried in a gaseous oxidising medium at a temperature between about 200–350° C. Alternatively, the oxides are heated in a gaseous oxidising medium to approximately 400° C. before being slowly cooled to room temperature while being rotated in a magnetic field. Typically, the magnetic field has a rotational frequency of about 60 r.p.m. and a field strength of about 3 kOe.

In one form of the invention, the hydroxides are precipitated in conditions which cause the precipitated hydroxides to contain 1–20 atomic percent of iron in the trivalent form, the remainder being in divalent form. In a more specific form of the invention, the hydroxides are precipitated in conditions which cause the precipitated hydroxides to contain 5–15 atomic percent of iron in the trivalent form, the remainder being in divalent form.

The water-soluble salt of iron used in the preparation of the aqueous solution may be organic or inorganic. For example, the water-soluble salt of iron used in the preparation of the aqueous solution may be iron sulphate.

The water-soluble salt of cobalt or each alternate metal ion used in the preparation of the aqueous solution may also be organic or inorganic. Where the further alternate ion is cobalt, the water-soluble salt may be cobalt sulphate.

The co-precipitation of the hydroxides may be induced by the addition of an alkaline agent such as an alkali or alkaline earth metal hydroxide.

Typically, the co-precipitation of hydroxides is carried out at 5–30° C.

Suitable oxidising agents include nitrates, such as potassium-, sodium-ammonium-nitrate, water soluble chlorates, such as sodium chlorate, persulfates such as sodium persulfate, $H_2O_2$ and oxygen.

The oxidation of the co-precipitated hydroxides is advantageously carried out at temperatures between about 50° C. and the boiling point of the solution. In a specific form of the invention, oxidation of the co-precipitated hydroxides takes place at temperatures of about 65–90° C.

In a further embodiment there is provided a method for production of a magnetic material within the scope of the invention, the method comprising the steps of:

(i) Procurement of non-magnetic cubic precursor particles;

(ii) Coating of the non-magnetic cubic precursor particles to prevent sintering of the particles;

(iii) Reduction of the non-magnetic cubic precursor particles to magnetite; and (iv) Oxidization of magnetite to γ-ferric oxide (γ-$Fe_2O_3$).

An example of a non-magnetic cubic precursor particles is haematite particles.

Methods for Precipitation of Haematite Precursors

1 In a first method for precipitation of uniform α-$Fe_2O_3$ particles, a dilute solution of an iron(III) salt was heated at reflux in dilute acid for at least 24 hours. The iron(III) salt used was the chloride salt. Nitrate or perchlorate salt can also be used. The corresponding acid used was hydrochloric acid. However nitric or perchloric acid are also appropriate. 0.4 mol/L $FeCl_3$ (10 ml), 0.032 mol/L HCl (25 ml) and D.I. water (365 ml) were preheated to ~100 deg. C., then mixed and maintained at reflux for 48 hours. The resulting precipitate was collected by centrifugation and washed by repeated centrifugation/re-suspension cycles in D.I. water, or by dialysis with D.I. water for a period of days.

2 In a second method for precipitation of uniform α-$Fe_2O_3$ particles, a concentrated iron(III) hydroxide gel was aged for a period of days at ~100 deg. C. The hydroxide gel was formed by mixing an equivalent amount of a strong base, being sodium hydroxide with a solution of an iron(III) salt. Potassium hydroxide is another strong base which can also be used for mixing with a solution of an iron (III) salt. 6.0 mol/L NaOH solution (65 ml) was slowly added to a stirred solution of 2.0M $FeCl_3$ (65 ml) in a 125 ml Erlenmeyer flask. The flask was then sealed and placed in an oven, preheated to 100° C., for 24 hours. The resulting precipitate was collected by centrifugation and washed by repeated centrifugation/re-suspension cycles in D.I. water, or by dialysis with D.I. water for a period of days.

Surface Treatment and Drying

In order to prevent sintering of non-magnetic cubic precursor particles during reduction, the particles can be coated with a surfactant such as oleic acid, stearic acid or other long-chain carboxylic acids. Other anionic surfactants such as sodium dodecyl benzene sulphonate (SDBS) may also be used.

Method for Surface Treatment and Drying

A haematite suspension (100 ml) containing about 0.25 g α-$Fe_2O_3$ was warmed to about 60 deg. C with stirring and rendered basic (~pH 11) by addition of a little NaOH solution (1 mol/L). A 1% (w/w) solution of sodium stearate (5 ml) was added and the suspension stirred and heated gently for a further 15 minutes. The mixture was then acidified by addition of HCl and transferred to a separating funnel and when cool, the stearate-coated α-$Fe_2O_3$ is extracted into 130 ml hexane. After washing excess stearic acid from the organic phase with a few aliquots of D.I. water, the hexane phase is evaporated to dryness at 50–70° C. under reduced pressure.

Reduction of Haematite to Magnetite

Non-magnetic cubic precursor particles such as α-$Fe_2O_3$ may be converted to magnetic $Fe_3O_4$ by heat treatment in a reducing gas such as hydrogen or carbon monoxide. The reduction may be carried out at temperatures between 350 and 450° C. and at gas flow rates of 100 ml/min or greater. Ideally the reduction is carried out in an atmosphere of 5% hydrogen and 95% nitrogen at a temperature of 400° C. over a period of at least 1 hour.

Oxidation of Magnetite

Oxidation of magnetite to γ-$Fe_2O_3$ is carried out by heat treatment in an oxidising gaseous medium. The magnetite may be dried in a gaseous oxidising medium at a temperature between about 200–350° C. Alternatively, the magnetite is heated in a gaseous oxidising medium to approximately 400° C. before being slowly cooled to room temperature while being rotated in a magnetic field. Typically, the magnetic field has a rotational frequency of about 60 rpm and a field strength of about 3 kOe.

The present invention further provides an improved method for site specific treatment of diseased tissue in a patient, which comprises the steps of:

(i) delivering the magnetic material of the present invention to diseased tissue in a patient; and (ii) exposing the magnetic material in the patient to a cyclic magnetic field with a frequency of greater than about 20 kHz and a field strength selected such that the product of field strength, frequency and the radius of the exposed region is less than about $7.5 \times 10^7$ A/s to generate hysteresis heat in the diseased tissue.

Preferably, step (ii) is carried out for sufficient time to generate enough heat from the administered magnetic material to raise the tumour temperature above about 42° C. It will be appreciated that the amount of time for treating a tumour will largely depend on the size, position and physical structure of the tumour. Most preferably step (ii) is repeated until the diseased tissue has been destroyed or treated sufficiently to ameliorate the disease.

The method of the invention provides a means to increase temperature in the area of diseased tissue to above 41° C. to decrease the viability of malignant cells. A decrease in the viability of malignant cells results in either cell death or increased cell sensitivity to the effects of ionising radiation or chemotherapeutic drugs.

During treatment, patients are placed into a machine that generates a cyclic magnetic field. The cyclic magnetic field could be, for example, either a linear alternating magnetic field or a rotating magnetic field of strength H and frequency f.

In a linear alternating magnetic field the amplitude of the field varies sinusoidally along a fixed directional axis between a maximum positive amplitude and a maximum negative amplitude at a frequency of f. The magnetic field strength as a function of time, $H_a(t)$, is described mathematically by $$H_a(t) = H_a \sin(2\pi f t) \quad (1)$$

where $H_a$ is the magnetic field amplitude.

A rotational magnetic field can be described mathematically as the superposition of two orthogonal linear alternating magnetic fields with a $\pi/2$ phase difference, i.e.

$$H_r(t) = H_x \sin(2\pi f t) + H_y \sin(2\pi f t + \pi/2) \quad (2)$$

where $H_y$ and $H_y$ are the amplitudes of linear alternating magnetic fields directed in the X and Y directions respectively which combine to give $H_r$ and f is their frequency of alternation. In this case the amplitude of the field remains constant but the direction of the field rotates with angular frequency of $2\pi f$. An advantage of the use of a rotational magnetic field compared to a linear alternating magnetic field of the same frequency and amplitude is that it leads to higher magnetic heating efficiency of the magnetic materials under some conditions. This in turn means that lower frequency and field strengths can be used in the method, if desired.

In order that enough hysteresis heat is generated by the magnetic material the cyclic magnetic field used in the method desirably has a relatively high frequency. The higher the frequency the greater the rate of heating in the tissues that contain the magnetic material. However, the physiological response to high amplitude, high frequency magnetic fields limit the field amplitude and frequency that can be used in any clinical application. These limitations result from nerve muscle activation and eddy current heating which depends, inter alia, on the electrical conductivity of the tissue. Both of these are as a result of the electric fields induced in the tissue by the magnetic field.

Preferably, the magnetic material is mixed in a liquid emulsion or is formed into microcapsules which may then be mixed with a suitable biocompatible medium for delivery into a patient. Most preferably the magnetic material is bound in a matrix material to form a microcapsule. Most magnetic particles themselves are, typically, too small and too dense to enable optimum delivery to the site of diseased tissue. Therefore, they are desirably encapsulated in microcapsules. Important properties of microcapsules are their density and their diameter. The density affects the efficiency of their carriage by the blood stream to the site of immobilisation in the diseased tissues vascular network while the size determines the proximity of the point of immobilisation to the diseased tissue.

Preferably, the magnetic material is bound in a matrix material which does rot adversely affect the hysteresis or eddy current heating properties of the magnetic particles. The non-toxic binder or matrix material may comprise any of the suitable non-toxic materials which are well known in the microencapsulation art. Suitable materials include, for example, proteins, polymeric resins such as styrene-divinylbenzene, biopol, albumin, chitosan etc.

In a preferred form of the invention, the microcapsules are adapted to bind or absorb or contain a cytotoxic material which is released upon heating of the microcapsule. For example the microcapsule may be composed of a porous, heat sensitive material which is non-toxic to and, preferably, inert to or compatible with animal tissue and which has embedded within it suitable magnetic material. The pores in the material are desirably filled with the cytotoxic compound. Upon hysteresis heating the micro-particles are capable of expanding, thereby permitting the release of the cytotoxic compound. Such particles should, however, be resistant to melting upon hysteresis heating. Thus, the use of such particles in the method of the present invention provides a single device with which combined chemotherapy and thermotherapy can be achieved to treat diseased tissue in a patient.

Another alternative delivery technique could be the injection or intra-vascular infusion of a suitable ferrocolloid which could consist, for example, of a suspension of magnetic microparticles in a liquid medium such as lipiodol. In this case the magnetic particles could range in size from subdomain nanometer size up to several microns.

A combination of different types of microcapsules may also be administered at the time of treatment to provide a multimode treatment. Microcapsules may be either radioactive microcapsules or chemotherapeutic microcapsules together with the hyperthermic microcapsules described. Further, the targeted hyperthermia therapy may be used in conjunction with conventional radiotherapy and/or chemotherapy. The choice of treatments will depend upon the specific details of each case as it presents.

According to a further embodiment of the invention, an ionising radiation source may be applied to the locus of the diseased tissue in conjunction with a magnetic field, said tissue having microcapsules as herein described included therein. The radiation source may be microcapsules which contain a radioactive compound such as Yttrium-90 or delivered from an external radiation source. An additional application of magnetic materials with the properties described in this application would be for use in antipilferage devices, or Electronic Article Surveillance (EAS) devices. Here, a magnetically very soft material is combined with a semi-hard material to make a label or tag that can be attached to an article in, say, a shop or library. If an attempt is made to move the article through a detection gate without first deactivating the tag then an alarm is sounded. The tags are deactivated by magnetising the semi-hard material using a deactivator tablet that contains strong permanent magnets. The semi-hard magnetic material may also be used to provide a permanent bias field for the soft component. The magnetic characteristics of the magnetic materials described in this patent application make them well suited for use as the semi-hard component of the antipilferage devices.

BEST MODE(S) FOR CARRYING OUT THE INVENTION

Figure 1:
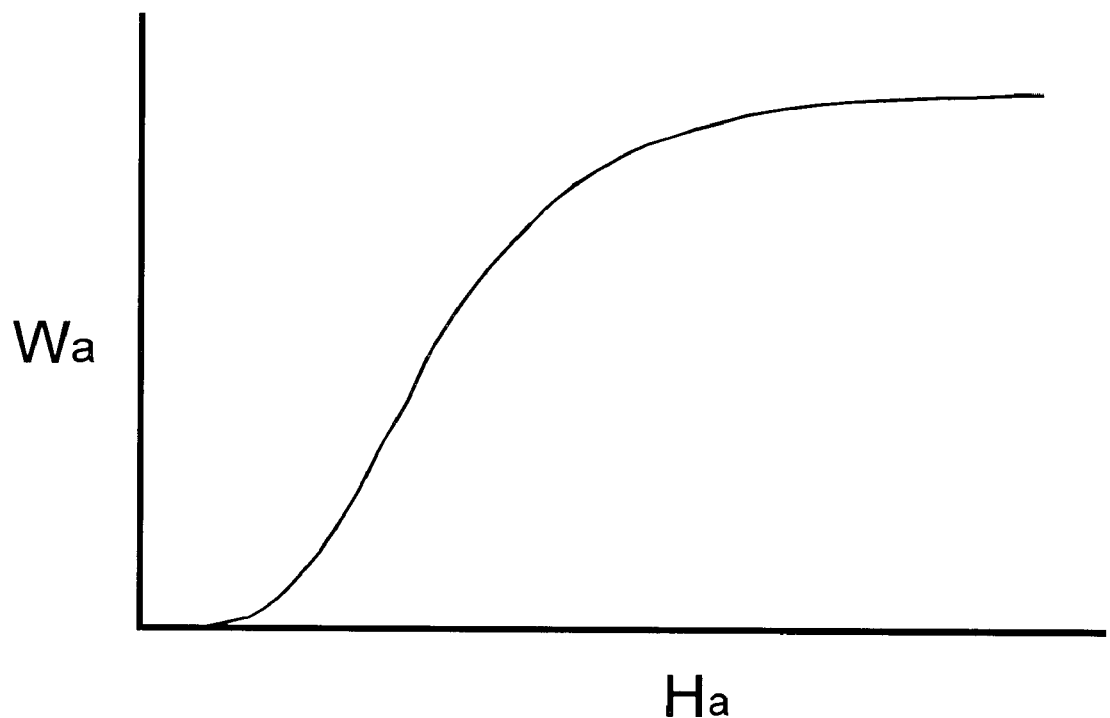
FIG. 1 illustrates a typical form of alternating hysteresis work per cycle, $W_a$, as a function of applied field, $H_a$.
Figure 2:
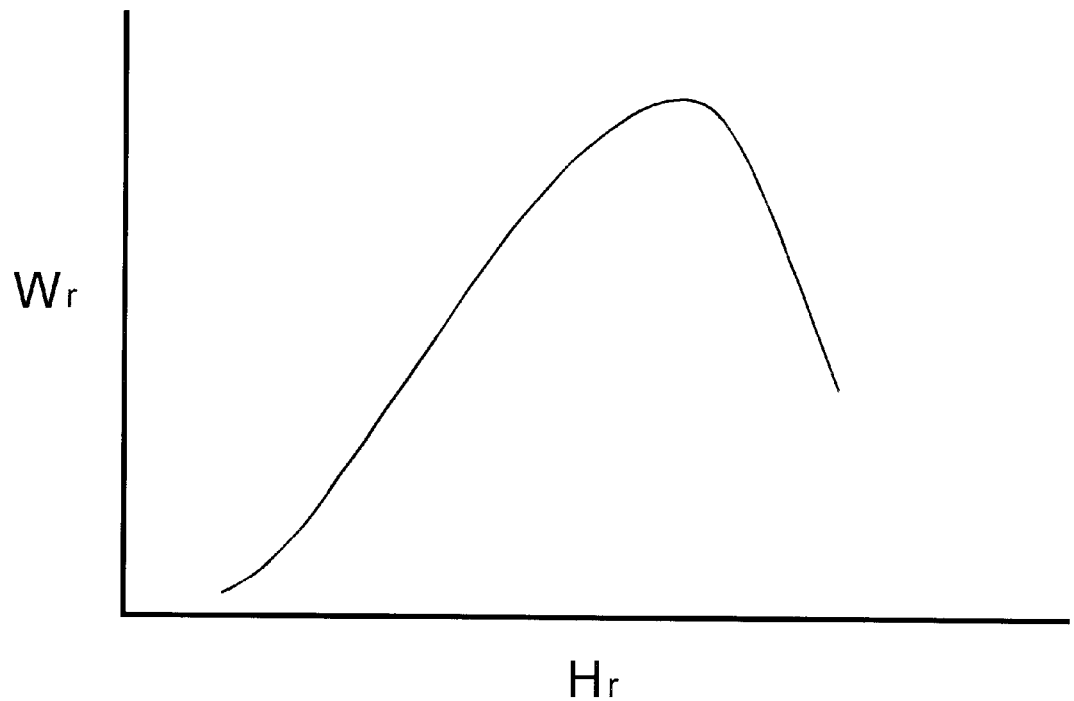
FIG. 2 illustrates a typical form of rotational hysteresis work per cycle, $W_r$, as a function of applied field, $H_r$.

Features of the present invention are more fully described in the following examples. It is to be understood that the following examples are included solely for the purposes of exemplifying the invention, and should not be understood in any way as a restriction on the broad description as set out above.

EXAMPLE 1

Preparation

To a solution of 7 moles NaOH and 0.04 moles $NaClO_3$ in 6 liters of water, which is kept under argon, there is quickly added at room temperature (22° C.) a solution of 2.965 moles of $FeSO_4 \cdot 7H_2O$ and 0.035 moles of $CoSO_4 \cdot 7H_2O$ in 3 liters of water. The precipitate of hydroxides formed contains 3 moles of metal atoms of which 1.17 atomic percent is cobalt. The suspension is heated under argon to 80° C. and mixed with 1 moles of $NaNO_3$ in 0.3 liters of water. The mixture is kept at 80° C. while stirring for 80 minutes and heated to the boil for at least 60 minutes. The precipitate is washed 4 times with deionised water and vacuum dried at 100° C. The dried precipitate is oxidised by heating it under a stream of air to 280° C. After 6 hours the black precipitate is transformed into a greyish brown oxide corresponding approximately to the formula $Me_2O_3$, in which Me represents iron and/or cobalt.

Magnetic Properties

This oxide has the following magnetic values; remanence=22 emu/g, coercivity=165 Oe. These values were measured using a Vibrating Sample Magnetometer (VSM) with a saturating field of +/−10 kOe and a magnetic field ramp rate of 50 Oe/s. The sample for magnetic measurement was prepared by dispersing under 2% by volume of oxide powder in molten wax in a plastic sample holder of 5.4 mm internal diameter by 6 mm long.

Measurement of the MHE of this material as a function of applied field strength in a rotating magnetic field show that the MHE is $5.25 \times 10^{-8}$ J.m/A.g when the applied field is 25 kA/m and the frequency is 20 kHz, a value in excess of the desired minimum of $4.5 \times 10^{-8}$.

Comparison to existing materials

Table 1 lists the maximum experimentally measured values of Magnetic Heating Efficiency for a number of commercially available materials for applied rotating magnetic fields up to 25 kA/m, the maximum field that can be used in order to comply with the preferred field conditions described above. The results for the commercially available materials are compared to the oxide of Example 1 which shows the highest MHE of all.

TABLE 1

| Magnetic Material | Source | MHE (J · m/A · g) |
| --- | --- | --- |
| Co-$\gamma Fe_2O_3$ (S11) | Bayer Chemicals | $2.5 \times 10^{-8}$ |
| $\gamma Fe_2O_3$ | BASF | $0.8 \times 10^{-8}$ |
| Magnetite | Magnox | $3.25 \times 10^{-8}$ |
| Alnico | Crumax Magnetics | $3.1 \times 10^{-8}$ |
| Chromium Dioxide | BASF | $0.25 \times 10^{-8}$ |
| Co—$Fe_3O_4/Fe_2O_3$ | BASF | $<0.5 \times 10^{-8}$ |
| Co-$\gamma Fe_2O_3$ (Example) | Paragon Medical | $5.25 \times 10^{-8}$ |

It is envisaged magnetic material of the present invention microparticles may be formulated in such a way as to regulate the temperature of the tumour to some predetermined maximum. This could be achieved by incorporating ferromagnetic materials with a Curie temperature, a compensation temperature, a martensitic transformation or some other suitable magnetic transformation at the required temperature, called $T_c$, into the microparticles. The requirement would be that a suitably large MHE is available for $T<T_c$ and MHE≈0 for $T>T_c$.

EXAMPLE 2

Example Showing Effect of Particle Size, Coercivity and Loop Squareness on MHE

Figure 3:
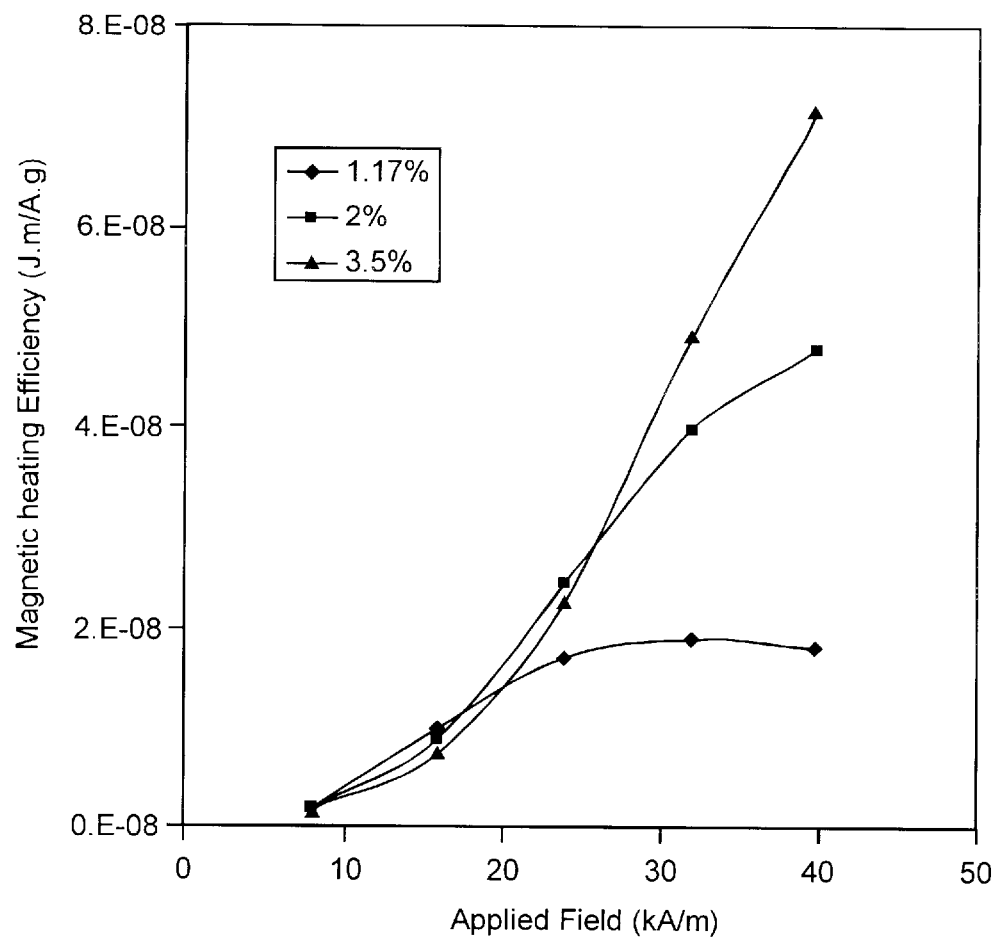
FIG. 3 shows MHE data measured for 3 different batches of particles in which different amounts of cobalt have been substituted for iron atoms. Data is for alternating fields only.
Figure 4:
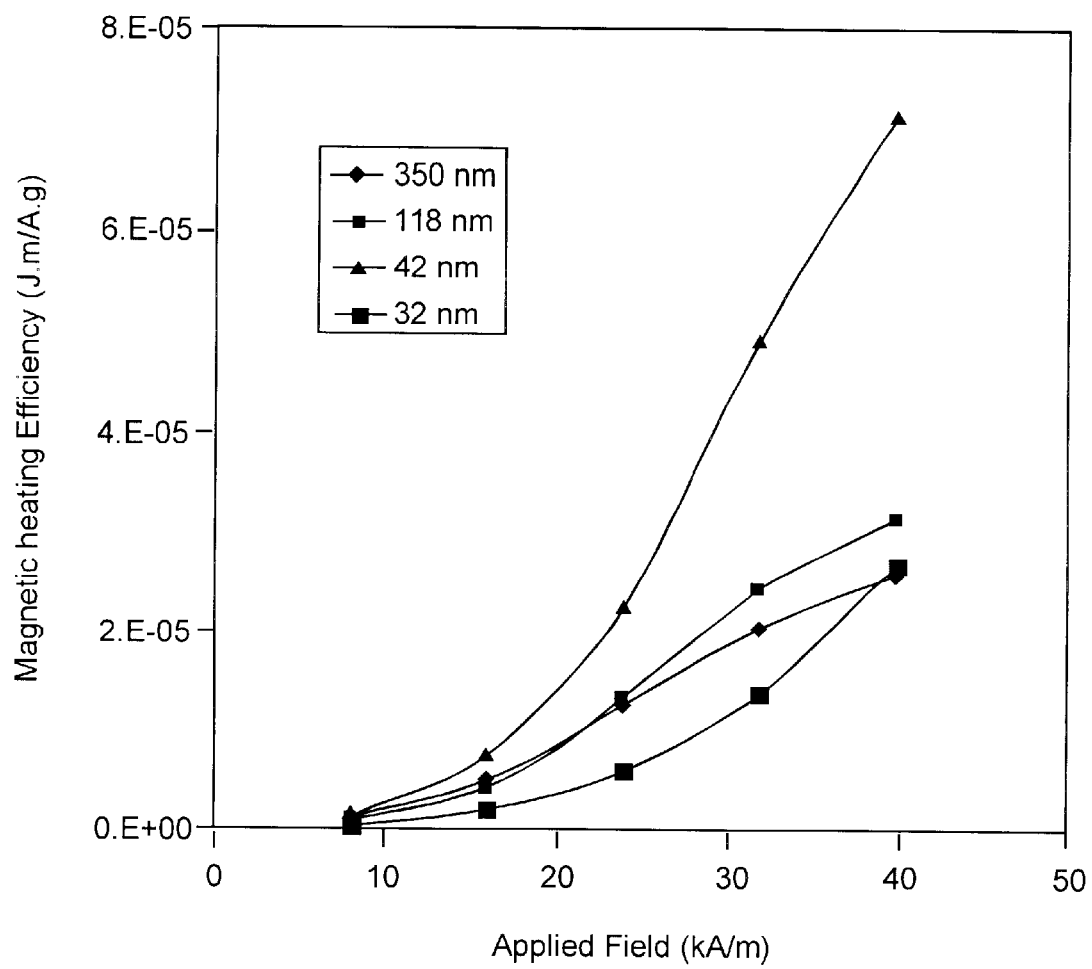
FIG. 4 shows MHE data measured for particles with the same level of cobalt doping but of different average size. Data is for alternating fields only.

FIGS. 3 and 4 show the MHE as a function of applied field inferred from VSM measurements on several batches of magnetic particles fabricated using the method described in the first example. These MHE results are for the case of alternating fields only.

FIG. 3 shows MHE data measured for 3 different batches of particles in which the level of substitution of cobalt for iron atoms has been varied. The different levels of cobalt also give rise to different coercivities and values of loop squareness. For 1.17% cobalt the coercivity is 145 Oe (11.5 kA/m) and loop squareness is 0.316; for 2% cobalt the coercivity is 208 Oe (16.6 kA/m) and loop squareness is 0.372; for 3.5% cobalt the coercivity is 304 Oe (24.2 kA/m) and loop squareness is 0.503. In all cases the average particle size is approximately 40 nanometers. These data show a general trend of increasing MHE with improved loop squareness.

FIG. 4 shows MHE data measured for particles with the same level of cobalt doping but of different average particle size. Once again coercivity and loop squareness also varies with particle size. For the 350 nm particles coercivity is 200 Oe (15.9 kA/m) and loop squareness is 0.276; for 118 nm particles the coercivity is 241 Oe (19.2 kA/m) and loop squareness is 0.398; for 42 nm particles the coercivity is 304 (24.2 kA/m) and loop squareness is 0.503; for 32 nm particles the coercivity is 460 Oe (36.6 kA/m) and loop squareness is 0.528. Again the better the loop squareness then the better is MHE except when coercivity is too great compared to the applied field as is the case for the 32 nm particles.

These examples show how the level of cobalt doping and particle physical parameters can be varied to maximise the MHE. Note that the MHE achieved by these materials up to an applied field of 25 kA/m does not reach the same level as for the material shown in example 1 for a rotating magnetic field.

It should be understood that the foregoing description of the invention including the principles, preferred embodiments and Examples cited above are illustrative of the invention and should not be regarded as being restrictive on its scope. Variations and modifications may be made to the invention by others without departing from the spirit of that which is described as the invention and it is expressly intended that all such variations and changes which fall within this ambit are embraced thereby is intended merely to be illustrative thereof.

What is claimed is:

1. A magnetic material having a magnetic heating efficiency of at least $4.5 \times 10^{-8}$ J.m/A.g in a cyclic magnetic field where the product of the amplitude and frequency of the applied field is less than or equal to $5 \times 10^8$ A/m.s, and the frequency of the applied field is at least 20 kHz and wherein (i) the magnetic material is a substituted magnetite ($Fe_3O_4$) or gamma ferric oxide ($\gamma$-$Fe_2O_3$) crystalline lattice in which some of the iron atoms in that crystalline lattice have been substituted for one or more alternate metal atoms and (ii) the magnetic material has a predominantly cubic magnetocrystalline anisotropy.

2. A magnetic material according to claim 1 wherein the magnetic material is provided in particulate form, with particles possessing equant morphology.

3. A magnetic material according to any one of claim 2 wherein the particles are of a size between 20 nm and 1 $\mu$m.

4. A magnetic material according to claim 2 characterised by loop squareness of between 0.5 and 1 with coercivity of 25 kA/m or less and high saturation magnetism.

5. A magnetic material according to claim 1 wherein the magnetic material has a coercivity of less that 314 Oe.

6. A magnetic material according to claim 5 wherein the coercivity is less than 200 Oe.

7. A magnetic material according to claim 1 wherein the substituting metal atoms are selected from a group consisting of cobalt, zinc, nickel, manganese, magnesium, copper, chromium, gallium, and cadmium.

8. A magnetic material according to claim 7 wherein the substituting metal atoms may either be selected entirely from the same atomic species or a plurality of different metal atoms can be incorporated into the crystalline lattice.

9. A magnetic material according to claim 7 wherein the substituting metal atoms are dispersed in a substantially even manner throughout the crystalline lattice.

10. A magnetic material according to claim 7 wherein the substituting metal atom is cobalt.

11. A magnetic material according to claim 10 wherein the degree of substitution with cobalt atoms is less than about 4% of the iron atoms in the crystalline lattice.

12. A magnetic material according to claim 11 wherein the degree of substitution with cobalt atoms is in the range of 0.2 and 3.5% of the iron atoms in the crystalline lattice.

13. A magnetic material according to claim 1 wherein the magnetic heating efficiency of that material is such as to enable production of sufficient heat to raise the temperature of the surrounding matter to 42° C.

14. A magnetic material according to claim 13 wherein the magnetic material is capable of producing at least 22.5 watts per gram of material when exposed to a cyclic magnetic field.

15. A magnetic material according to claim 13 wherein the magnetic material is delivered in the form of microcapsules to the site of cancer via intra-arterial infusion.

16. A microcapsule comprising a magnetic material according to claim 1 wherein the magnetic material is bound in a matrix material.

17. A microcapsule according to claim 16 wherein the magnetic material is bound in a matrix material which does not adversely affect the hysteresis or eddy current heating properties of the magnetic particles.

18. A microcapsule according to claim 16 wherein the matrix material is selected from a group comprising proteins, polymeric resins such as styrene-divinyl benzene, biopol, albumin and chitosan.

19. A microcapsule according to claim 16 wherein the microcapsules are adapted to bind or absorb or contain a cytotoxic material.

20. A microcapsule according to claim 19 wherein the cytotoxic material is released upon heating of the microcapsule.

21. A microcapsule according to claim 16 wherein the microcapsule is composed of a porous, heat sensitive material which is non-toxic and inert to or compatible with animal tissue and which has embedded within it suitable magnetic material.

22. A microcapsule according to claim 16 wherein the pores within the porous material are filled with a cytotoxic material.

23. A composition comprising (i) a magnetic material having a magnetic heating efficiency of at least $4.5 \times 10^{-8}$ J.m/A.g in a cyclic magnetic field where the product of the amplitude and frequency of the applied field is less than or equal to $5 \times 10^8$ A/m.s, and the frequency of the applied filed is at least 20 kHz and wherein (i) the magnetic material is a substitute magnetite ($Fe_3O_4$) or gamma ferric oxide ($\gamma Fe_2O_3$) crystalline lattice in which some of the iron atoms in that crystalline lattice have been substituted for one or more alternate metals atoms and (ii) the magnetic material has a predominately cubic magnetocrystalline anisotropy, or a microcapsule according to claim 16 and (ii) at least a microcapsule suspension selected from the group consisting of radioactive microcapsules or chemotherapeutic microcapsules.

24. A composition according to claim 23 wherein the radioactive microcapsules at least contain Yttrium-90 as the radiation source.

25. A composition comprising a magnetic material according to claim 1 in a liquid medium suspension.

26. A composition according to claim 23 wherein the liquid medium is lipiodol.

27. A method for site specific treatment of diseased tissue in a patient, which comprises the steps of:
   (i) delivering the magnetic material of anyone of claims 1 to 14 or the microcapsule according to anyone of claims 16 to 20 or the composition according to anyone of claims 23 to 26 to the diseased tissue in a patient; and
   (ii) exposing the magnetic material in the patient to a cyclic magnetic field with a frequency of about 20 kHz and a field strength selected such that the product of field strength, frequency and the radius of the exposed region is less than about $7.5 \times 10^7$ A/s to generate hysteresis heat in the diseased tissue wherein the magnetic material is a substituted magnetite ($Fe_3O_4$) or gamma ferric oxide ($\gamma$-$Fe_2O_3$) crystalline lattice in which some of the iron atoms in that crystalline lattice have been substituted for one or more alternate metal atoms and (ii) the magnetic material has a predominantly cubic magnetocrystalline anisotropy.

28. A method for site specific treatment of diseased tissue in a patient according to claim 27 wherein the magnetic material is provided in particulate form, with particles possessing equant morphology.

29. A method for site specific treatment of diseased tissue in a patient according to claim 27 wherein step (ii) is carried out for sufficient time to generate enough heat from the administered magnetic material to raise the diseased tissue temperature above about 42° C.

30. A method for site specific treatment of diseased tissue in a patient according to claim 27 wherein step (ii) is repeated until the diseased tissue has been destroyed or treated sufficiently to ameliorate the disease.

31. A method for specific treatment of diseased tissue in a patient according to claim 27 wherein the cyclic magnetic field is a linear alternating magnetic field of strength H and frequency f.

32. A method for site specific treatment of diseased tissue according to claim 31 wherein the radiation source may be microcapsules which contain a radioactive source such a Yttrium-90 or delivered from an external radiation source.

33. A method for specific treatment of diseased tissue in a patient according to claim 27 wherein the cyclic magnetic field is a rotating magnetic field of strength H and frequency f.

34. A method for site specific treatment of diseased tissue in a patient according to claim 27 wherein an ionizing radiation source is applied to the locus of the diseased tissue in junction with a magnetic field.

35. An antipilferage device comprising a magnetic material having a magnetic heating efficiency of at least $4.5 \times 10^{-8}$ J.m/A.g in a cyclic magnetic field where the product of the amplitude and frequency of the applied field is less than or equal to $5 \times 10^8$ a/m.s, and the frequency of the applied filed is at least 20 kHz and wherein (i) the magnetic material is a substitute magnetite ($Fe_3O_4$) or gamma ferric oxide ($\gamma Fe_2O_3$) crystalline lattice in which some of the iron atoms in that crystalline lattice have been substituted for one or more alternate metals atoms and (ii) the magnetic material has a predominately cubic magnetocrystalline anisotropy.

* * * * *